United States Patent [19]

Okarma

[11] Patent Number: 6,143,508
[45] Date of Patent: Nov. 7, 2000

[54] DEVICE AND PROCESS FOR CELL CAPTURE AND RECOVERY

[75] Inventor: Thomas B. Okarma, Palo Alto, Calif.

[73] Assignee: Rhone-Poulenc Rorer Pharmaceuticals Inc., Collegeville, Pa.

[21] Appl. No.: 08/484,559

[22] Filed: Jun. 7, 1995

Related U.S. Application Data

[63] Continuation-in-part of application No. 08/291,335, Aug. 17, 1994, which is a continuation of application No. 07/785,222, Oct. 28, 1991, abandoned, which is a continuation of application No. 07/638,030, Jan. 2, 1991, abandoned, which is a continuation of application No. 07/374,091, Jun. 29, 1989, abandoned.

[51] Int. Cl.$^7$ .......................... A61K 35/18; C07K 16/28; C12N 5/08
[52] U.S. Cl. .......................... 435/7.21; 435/7.1; 435/7.23; 435/7.24; 436/531; 436/824; 436/532; 424/93.7; 424/93.71; 530/388.7; 530/388.75; 530/389.6
[58] Field of Search ................................ 435/7.21, 240.2, 435/240.25, 7.1, 7.23, 7.24; 436/531, 824, 532; 424/93.7, 93.71; 530/388.7, 388.75, 389.6

[56] References Cited

U.S. PATENT DOCUMENTS

| | | |
|---|---|---|
| 1,676,579 | 7/1928 | Sperti et al. . |
| 3,016,336 | 1/1962 | Scott et al. . |
| 3,645,849 | 2/1972 | Gray . |
| 3,956,219 | 5/1976 | Smithwick, Jr. . |
| 3,974,110 | 8/1976 | Patchornik et al. . |
| 4,250,139 | 2/1981 | Luck et al. . |
| 4,438,198 | 3/1984 | Schmer . |
| 4,460,445 | 7/1984 | Rekers . |
| 4,464,165 | 8/1984 | Pollard, Jr. . |
| 4,497,796 | 2/1985 | Salser et al. . |
| 4,614,513 | 9/1986 | Bensinger . |
| 4,620,908 | 11/1986 | Van Duzer . |
| 4,654,299 | 3/1987 | Lentfer . |
| 4,690,915 | 9/1987 | Rosenberg . |
| 4,699,877 | 10/1987 | Cline et al. . |
| 4,714,680 | 12/1987 | Civin . |
| 4,727,027 | 2/1988 | Wiesehahn et al. . |
| 4,736,019 | 4/1988 | Bellattar et al. . |
| 4,933,410 | 6/1990 | Okrongly . |
| 5,081,029 | 1/1992 | Zarling et al. . |
| 5,081,030 | 1/1992 | Civin . |
| 5,126,132 | 6/1992 | Rosenberg . |
| 5,215,926 | 6/1993 | Etchells, III et al. .................. 436/501 |
| 5,241,012 | 8/1993 | Clark .................................... 525/333.6 |

FOREIGN PATENT DOCUMENTS

| | | |
|---|---|---|
| 0 140 489 | 5/1985 | European Pat. Off. . |
| 0294059 | 12/1988 | European Pat. Off. . |
| 2-150274 | 6/1990 | Japan . |
| WO 87/04628 | 8/1987 | WIPO . |
| WO 88/01642 | 3/1988 | WIPO . |
| WO 88/04692 | 6/1988 | WIPO . |

OTHER PUBLICATIONS

Rutishauser, Urs, "Specific Fractionation and Manipulation of Lymphocytes with Derivatized Nylon Fibers," *Immunochemistry*, vol. 12, pp. 603–606 (1975).
Tijssen, P., "The Immobilization of Immunoreactants on Solid Phases," in *Laboratory Techniques in Biochemistry and Molecular Biology, vol. 15, Practice and Theory of Enzyme Immunoassays*, Burdon et al., Eds., Elsevier, New York, pp. 305–309, (1985).
Lotze, Michael, "Transplantation and Adoptive Cellular Therapy of Cancer: The Role of T–Cell Growth Factors," *Cell Transplantation*, vol. 2, pp. 33–47, (1993).
Whiteside et al., "Tumor–Infiltrating Lymphocytes: Their Phenotype, Functions and Clinical Use," *Cancer Immunol. Immunotherapy*, vol. 39, pp. 15–21 (1994).
Basch et al., "Cell Separation Using Positive Immunoselective Techniques," *Journal of Immunological Methods*, vol. 56, pp. 269–280 (1983).
Leivestad et al., "Positive selection of activated T cells of the T8 (CD8) sub–type by immunomagnetic separation," *Tissue Antigens*, vol. 28, pp. 46–52 (1986).
English Abstract of JP 2–50112.
English Abstract of JP 59–113898.
Affinity Chromatography: Principles and Methods, Pharmacia Fine Chemicals, Uppsala, 1979, pp. 96–97.
Andrews, R.G., et al., *Blood* (1986) 67:842–845.
Antin, J., et al., *Blood* (1991) 78(8); 2139–2149.
Antman, K., and Gale, R.P., *Breast Cancer Res and Treatment* (1978) 10:88.
Antman, K., and Gale, R.P., *Ann. Int. Med.* (1988) 108:570–574.
Antman, K., et al., *J Clin Oncol* (1992) 10:102–110.
Armitage, J.O., *Blood* (1991) 77:211–213).
Ball, E.D., et al., *Blood* (1986) 68:1311–1315.
Beschorner, W.E., et al., *AJP* (1985) 119:1–4.
Bidey, S., "Immobilized Mammalian Cells in Hormone Detection and Quantitation," *Immobilized Cells and Enzyme: A Practical Approach*, J. Woodward, Ed. IRL Press, Washington, DC, pp. 150–151 (1985).
Blaise, D., et al., *Blood* (1990) 76:1092–1097.
Boon et al., *Int. J. Cancer* (1993) 54:177–180.
Broxmeyer, H.E., et al., *Proc. Natl. Acad. Sci. USA* (1989) 86:3828–3832.

(List continued on next page.)

*Primary Examiner*—Phuong T. Bui
*Attorney, Agent, or Firm*—Morrison & Foerster LLP

[57] ABSTRACT

Devices, processes and compositions are provided for effective separation of cells from a mixture of cells, where depletion or positive selection may be employed to provide a cellular population of interest. Of particular utility is the separation of cells from peripheral blood mononuclear cells, where members of the lymphoid or myeloid lineages may be isolated and used for research, diagnosis or therapy. Also of interest are cellular separation from bone marrow, tumor suspensions or lymphoid tissue suspensions, where cells can be isolated and used for a variety of purposes. The separated cells may be homogeneous, free of exogenous biologicals, viable, capable of replication and exhibit their full complement of biological activities. Multiple phenotypes can be captured simultaneously. Captured cells can be specifically activated with cytokines and antigens to provide cells which are MHC restricted and have antigen-specific effector functions.

28 Claims, 2 Drawing Sheets

OTHER PUBLICATIONS

Burnett, A.K., et al., *Lancet* (1984) ii:1068–1070.
Callegaro et al., "Hollow Fiber Immobilized L–asparaginase: In Vivo and In Vitro Immunological Studies," *International Journal Artif. Org.* (1983) 6(2):91–96.
Cardoso, A.A., et al., *Proc. Natl. Acad. Sci. USA* (1993) 90:8707–8711.
Champlin, R., ed., Bone Marrow Transplantation; Kluwer Acad. Pub., Boston, (1990) 99–111.
Champlin, R., et al., *Blood* (1990) 76(2):418–423.
Champlin, R.E., *Hem/Onc Clinics of No. Am.* (1990) 4:687–698.
Cheson, B.D., et al., *Ann Intern Med* (1989) 110:51–65.
Chu et al., "Protein–reactive, Molded Polystyrene Surfaces Having Applications to Immunoassay Formats," *J. Appl. Poly. Sci.*, (1987) 34:1917–1924.
Civin, C.I., et al., *J Immunol* (1984) 133:157–165.
Civin, C.I., et al., Bone Marrow Purging and Processing, pp. 387–402 (Wiley–Liss, New York, 1989).
Cote, R.J., et al., *Am J. Surg Pathol* (1988) 12(5):333–340.
Eder, J.P., et al., *J. Clin. Oncol.* (1986) 4:1592–1597.
Elias, A., et al., *Blood* (1992) 79:3036–3044.
Favrot, M.C. et al., *Brit J. Haem* (1986) 64:161–168.
Fei, et al., *Exp Hematol* (1990) 18(8):953–57.
Foon, *Cancer Research* (1989) 49:1621–1639.
Freshney, "Culture of Animal Cells," Alan R. Liss, New York (1987) p. 129.
Funderud, et al., in "Lymphocytes, A Practical Approach," (1987) Klaus, ed., IRL Press, Oxford, Washington, DC pp. 62–65.
Gale, R., et al., *Bone Marrow Transplantation* (1992) 9:151–155.
Gansbacher et al., *J. Exp. Med.* (1990) 172:1217–1224.
Geppert, et al., *Journal of Clinical Investigation* (1988) 81:1497–1505.
Gianni, A., et al., *Lancet* (1989) 2:580–584.
Goldstone, A.H., et al., *Brit J. Haematol* (1986) 64:529–537.
Gorin, N.C., et al., *Blood* (1986) 67:1367–1376.
Gottlieb, D.J., et al., *Blood* (1989) 74:2235–2342.
Gulati, S.C., Purging in Bone Marrow Transplantation (1993) R.G. Landes Co., pp. 24–29.
Hatzfeld, J., et al., *J. Exp. Med.* (1991) 174:925–929.
Haylock, D.N., et al., *Blood* (1992) 80:1405–1412.
Henslee, P.J., et al., *Transplanation Proc.* (1987); XIX(1):2701–2706.
Higuchi, C.M., et al. *Blood* (1991) 77:2561–2568.
Higuchi, C.M., et al., *Cancer Research* (1989) 49:5509–5513.
Hunt, in Handbook of Experimental Immunology, (2) *Cellular Immunology*, (1986) Weir et al. (editors), 4th ed., Blackwell Scientific Publications; Oxford, pp. 55.7–55.8.
Jones, R.J., et al., *Bone Marrow Transplanation* (1990) 5:301–307.
Kaizer, H., et al., *Blood* (1985) 65:6 1504–1510.
Keever, C.A. et al., *Blood* (1989) 73(5):1340–1350).
Kennedy, M.J., et al., *J. Natl. Cancer Inst.* (1991) 83:920–926.
Kernan, N.A. *Blood* (1991) 78(10 suppl. 1):77a, Abstract No. 298.
Kersey, J., et al., *N Eng J. Med* (1987) 317:461–467.

Kessinger, A., "Reestablishing Hematopoiesis after Dose Intensive Therapy with Peripheral Stem Cells," in Kessinger, A., J.O., Antman, K.A., eds., High–Dose Cancer Therapy, Pharmacology, Hematopoietins, Stem Cells., Williams & Wilkins, Philadelphia, 1992.
Kessler et al., "Large–Scale Purification and Characterization of CD34–Positive Hematopoietic Progenitor Cells," *Blood*, vol. 70 Supplement 1, p. 321a (1987).
Larsson et al., "Improved cell Depletion in a Panning Technique Using Covalent Binding of Immunoglobulins to Surface Modified Polystyrene Dishes," *J. Immunol. Methods* (1989) 116:293–298.
Linch, D.C., and Burnett, A.K., *Clinics in Hematology* (1986) 15:167–186.
Lu, L, et al., *J Immun* (1987) 139:1823–1829.
Mackinnon, S., et al., *Blood* (1990) 76:2037–2045.
Maraninchi, D., et al., *Lancet* (Jul. 25, 1987) 175–178.
Maraninchi et al., "Selective depletion of marrow T–cytotoxic lymphocytes (CD8) in the prevention of graft–versus––host disease after allogeneic bone–marrow transplant," *Transplant Int.* (1988) 1:91–94.
Menssen, et al., "Rapid dissociation of adherent human tumor cells by ultrasound," *J Immunol Meth* (1987) 104:1–6.
Miser, J., et al., *Proc Am Soc Clin Oncol* (1988) 7:999.
Morecki, S., et al., *Cancer Res* (1988) 48:4573–4577.
Morecki et al., *J. Biol. Resp. Modif.* (1990) 9:467–474.
Mumcuoglu, M., et al, *Exp. Hematol.* (1990) 18:55–60.
Okrongly, D.A. et al., *Blood* (1992) 80(10) Suppl. 1:373a.
Peterman et al., "The Immunochemistry of Sandwich–ELISAs," *J. Immunol. Methods* (1988) 111:217–275.
Peters, W.P., et al., *J.Clin. Oncol.* (1988) 6:1368–1376.
Peters, W.P., et al., *Blood* (1989) 74:50a (Suppl 1).
Prentice et al., "Depletion of T–lymphocytes in donor marrow prevents significant graft–versus–host disease in matched allogeneic leukaemic marrow transplant recipients," *Lancet* (Mar. 3, 1984).
Reisner, Y., et al., *Proc. Natl. Acad. Sci USA* (1980) 77:6778–6782.
Reisner, Y., et al., *Lancet* (1981) 2:327–331.
Reisner, Y., et al., *Blood* (1983) 61:341–348.
Reisner, Y., Gan, J., *Cancer Res.* (1985) 45:4026–4031.
Reittie, J.E., et al., *Blood* (1989) 73:1351–1358.
Ringden, O., et al., *Bone Marrow Transplantation* (1991) 7:221–226.
Rossi et al., "Immobilization of Arginase on Hollow Fiber Hemodialyzer," *International J. Artif. Org.* (1981) 4(2):102–107.
Sheridan, W., et al., *Lancet* (1992) 339:640–644.
Sieber, F., et al., *Proc. Natl. Acad. Sci. USA* (1984) 81:7584–7587.
Siena, S., *Blood* (1989) 74:1905–1914.
Simonsson, B., et al., *Leukemia* (1989) 3:631–636.
Slingluff et al., "Human Cytotoxic T Cells Specific for Autologuos Melanoma Cells: Successful Generation from Lymph Node Cells in Seven Consecutive Cases," *J Natl Cancer Inst* (1988) 80(13):1016–1026.
Soiffer, R.J., et al., *J. Clin. Oncology* (1992) 10(7):1191–1200.
Soiffer, R.J., et al., *Blood* (1992) 73:517–526.
Theobald, M. et al., *NEJM* (1992) 327(23): 1613–1617.
Thomas, T.E., et al., *J Immunol Methods* (1989) 120:221–231.
Thompson, J.A., et al., *J. Immunol.* (1986) 137:3675–3680.
Verfaillie, C., et al., *J. Exp. Med.* (1990) 172:509–520.

Wagner, J.E., et al., *J.Clin. Oncology* (1992) 10(5):779–789.
Walker, et al., *Science* (1986) 234:1563–1566.
Walker et al., "CD8+ Lymphocytes Can Control Acute HIV Infection of CF4+ T Cells," in Fifth International Conference on AIDS: The Scientific and Social Challenge, Abstract T.C.O. 32, International Development Research Centre, Ottawa (1989) p. 520.
Weinthal, J. et al., *ASCO Proceedings* (1992) 11:362.
Williams, S.F., et al., *J. Clin. Oncol.* (1989) 7:1824–1830.
Zanders et al., "Early Biochemical Events in T Lymphocytes Activated by Anti T3" in Human T Cell Clones, Feldmann et al., eds., Humana Press, Clifton, New Jersey (1985) pp. 209–217.
Belldegrun, A., et al., "Interleukin 2 Expanded Tumor–infiltrating Lymphocytes in Human Renal Cell Cancer: Isolation, Characterization, and Anti–tumor Activity," *Cancer Res* (1988) 48(1):206.
Blanchy et al., *J. Biomed. Mat. Res.* (1986) 20:469–479.
Cesar et al., "Sterilization of Biosensors," in Biosensors in Artificial Organs, Guilbeau et al., Eds., ASAIO Trans (1987) 33:840–845.
Civin, C.I., et al., *Prog. Clin. Biol. Res.* (1990) 333:387–402.
Davies, et al., *J Biol Chem* (1987) 262(20):9895–9901.
Davies, et al., *J Biol Chem* (1987) 262(20):9902–9907.
Davies, et al., *J Biol Chem* (1987) 262(20):9908–9913.
Edelman, G. M. et al., *Proc. Natl. Acad. Sci USA* (1971) 68(9):2153–2157.
Garrison, *Chem Rev* (1987) 87:381–398.
Kaushal, S. et al., "Pluripotent CD34 Stem Cells are not Susceptible to HIV Infection," *AIDS Weekly*, Oct. 31, 1994.
Klaus, G.G.B. ed., Lymphocytes: A Practical Approach, IRL Press, Oxford (1987) pp. 55–65.
Kondo et al. *Diabetes Care* (1982) 5(3):218–221.
Muul, L.M. et al., "Identification of Specific Cytolytic Immune Response Against Autologous Tumor in Humans Bearing Malignant Melanoma," *J Immunology* (1987) 138:989–995.
Oken, *Am J Clin Oncol (CCT)* (1982) 5:649–655.
Pole, J. et al., *J Clin Oncol* (1991) 9:152–158.
Sato et al., *Int. J. Art. Org.* (1985) 8(2):109–114.
Sato et al., *Int. J. Art. Org.* (1986) 9(2):131–136.
West, W.H. et al., *N. Engl. J. Med.* (1987) 316:898–905.
Woolston, *Med. Design & Material* (Jan. 1991) 1:42–51.
Seeger, R., et al., *Prog Clin Biol Res* (1991) 336:527–533.
Strauss, L.C., et al., *Exp Hematol* (1986) 14:878–886.

DEVICE AND PROCESS FOR CELL CAPTURE AND RECOVERY

This is a continuation-in-part of Ser. No. 08/291,335 filed Aug. 17, 1994, which is a continuation of Ser. No. 07/785,222 filed Oct. 28, 1991 and now abandoned, which is a continuation of Ser. No. 07/638,030 filed Jan. 2, 1991 and now abandoned, which is a continuation of Ser. No. 07/374,091 filed Jun. 29, 1989 and now abandoned. The disclosures of these applications are incorporated by reference.

TECHNICAL FIELD

The subject field concerns cellular separations employing devices having specificity for cell surface proteins. Particularly, the cellular source will be blood, spinal fluid, bone marrow, tumor homogenates, lymphoid tissue and the like.

BACKGROUND

There are numerous situations where it is of interest to isolate a specific class of cells or to remove a particular set of cells from a mixture of cells. Techniques which have been employed include fluorescence cell sorting, magnetic immunobeads, complement-mediated lysis, affinity chromatography, centrifugal elutriation and polystyrene panning of cells. Cells having substantial density differences, such as that between platelets and red cells can be grossly fractionated by gradient centrifugation methodologies. However, mammalian cells with equivalent densities, such as tumor cells, lymphocyte subsets, granulocytes, or stem cells, require some form of separation using molecular recognition of surface markers which correlate with their phenotype. Similarly, such molecular mechanisms are required to separate viruses and bacteria from one another in complex mixtures. Each of the aforementioned methods have serious drawbacks for many applications, where there is interest in isolation or removal of particular subsets of cells.

Disadvantages of fluorescence activated cell sorting for recovery of viable sorted cells are the slowness of the procedure, the fact that the isolated cells are coated with antibody, and the limited amounts of cells which can be obtained by the procedure.

With immunobeads, it is difficult to recover the cells from the beads after separation; the cells are frequently coated with antibody and magnetic beads, and distinct separations are only difficulty achieved. Complement mediated lysis is problematic for two reasons; first, depletion of target cells is incomplete, and second, non-target cells can be adversely affected by exposure to complement and the toxic by-products of target cell lysis. Affinity chromatography of cells using, for example, Sephadex G-10 coupled to antibody, suffers from poor recovery and inefficient depletion of target cells. Centrifugal elutriation is not capable of separating different phenotypic subpopulations of cells of like size.

The last methodology, panning developed by Wysocki and Sato, PNAS, 75:2844, (1978), utilizing passively absorbed antibody on polystyrene, is particularly inadequate. Only low recoveries can be achieved, and the process suffers from lack of specificity and contamination of the separated cells with antibody.

As the immune defense system becomes elucidated, it is increasingly evident that subsets of cells can have relatively narrow ranges of activities. Thus, subsets can be specialized for response to a particular disease, such as neoplasia, infection, viral or cellular, etc., response to transplants, and the like. It is therefore of great interest to be able to identify and purify these subsets of cells, not only to understand their action, but also to use these cells for prophylactic and therapeutic purposes. In order to achieve the desired results, it is necessary that substantially pure populations of the desired subset or subsets of cells can be obtained. Furthermore, the cells should be: (1) free of antibodies on their surface, (2) viable, (3) capable of fulfilling their normal function and (4) responsive to activation by biologicals in the same manner as normal cells in their normal environment.

SUMMARY OF THE INVENTION

Methods, compositions and devices are provided for the selective capture and release of biological particles capable of replication, particularly virus particles and cells. A medium containing the particles is contacted with a solid support having a high density of specific receptor sites, whereby particles having the complementary ligand become bound to the surface. The biological particles may be released from the receptors by either biological activation resulting in ligand shedding and release or physical means such as pipetting, mechanical vibration or ultrasonic sound, as appropriate. The cells can be numerically expanded, subjected to biologicals or other factors for differentiation and/or activation, or the like, and may be used for research, diagnostic, prophylactic and/or therapeutic purposes.

DESCRIPTION OF THE SPECIFIC EMBODIMENTS

Figure 1:
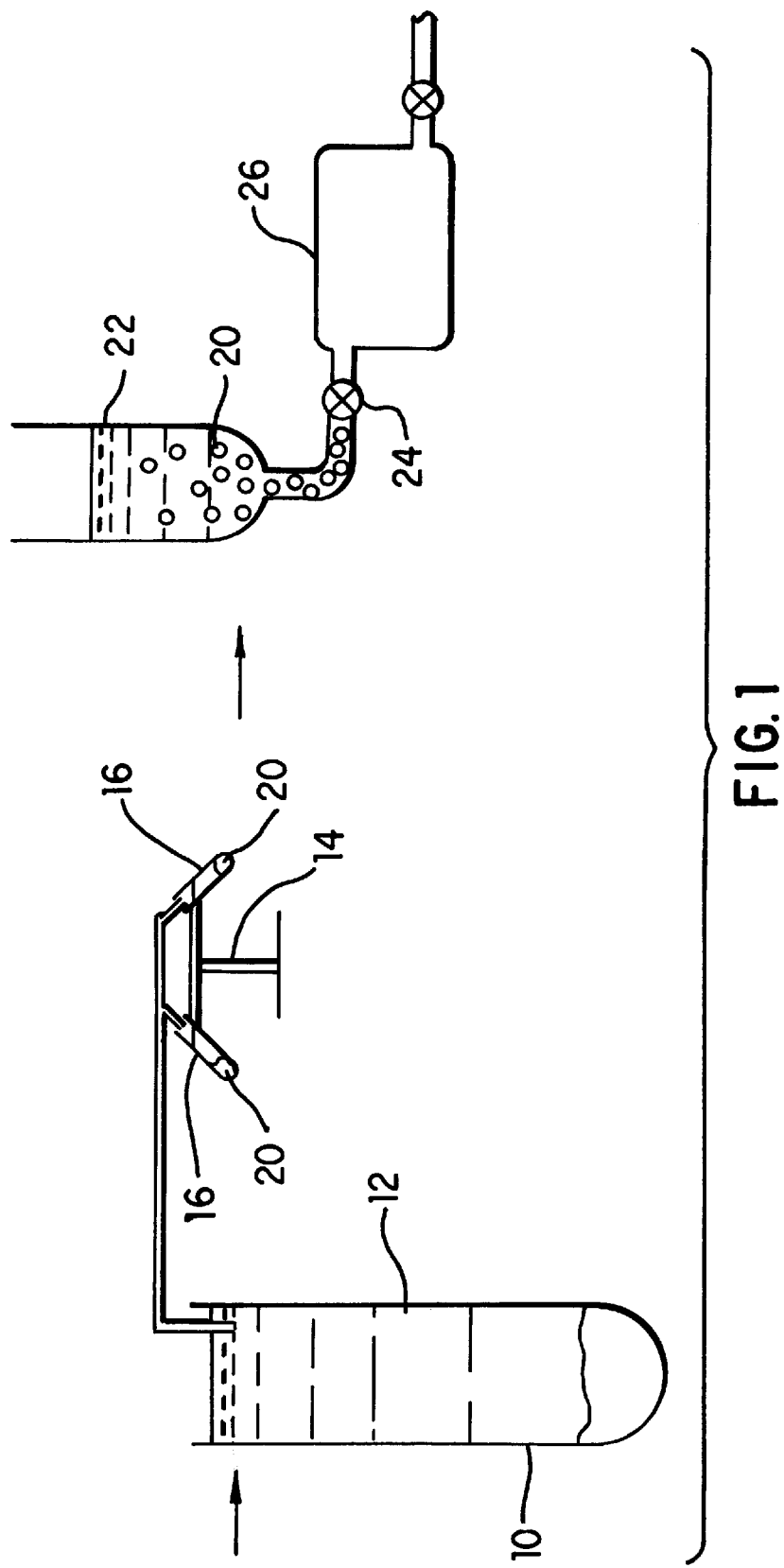
FIG. 1 is a schematic drawing of a process to prepare cells from peripheral blood or bone marrow for the capture device according to this invention.

Methods, composition and devices are provided for isolating a particular population of biologically replicatable particles, particularly cells, from a mixture of particles by binding the population to a solid substrate through the intermediacy of one or more specific receptors. Optionally, the particles may then be treated in a variety of ways to affect the population size and/or characteristics of the captured particles. The cells may then be released from the support substantially free of receptor.

The method will involve contacting a source of particles with receptor bound to a support in a collection device, where the population of the receptor on the surface provides for a high binding density for the ligand(s) of interest. The conditions for the contact are such as to allow for sufficient time and a low degree of turbulence to permit the particles to specifically bind to the receptor. After sufficient time for binding to occur, the medium may be removed and the surface washed to remove non-specifically bound particles. Since the particles will normally be bound to the surface at a plurality of sites, so as to have a high binding avidity, the washing may be fairly vigorous to insure the substantially complete removal of all non-specifically bound particles. The particles may then be subjected to a wide variety of conditions or treatments, usually involving contact with one or more reagents. Optionally, the medium containing the reagents may then be removed and the particles released from the receptors. Release may be achieved either by treatment with a combination of a mitogenic agent and a lymphokine or physical means such as pipetting, vibration or sonication. The particles may then be isolated and used for their intended purpose.

For the most part mixtures of cells will be employed and, therefore, the remaining discussion will be directed to cells. However, substantially the same procedures may be used for the isolation of virus and bacterial particles and in referring to cells, it should be understood that viruses and bacteria may usually be substituted therefore.

The subject device finds application in a number of different situations. The first is a situation in which one wishes to capture and remove undesirable cells from physiological fluids, thereby depleting the fluid of the undesirable cells for therapeutic benefit, or diagnostic or research applications. This may be illustrated by depleting bone marrow of certain T-lymphocytes to diminish graft-versus-host disease. The bone marrow, depleted of the unwanted cells, is immediately prepared for transplantation into the marrow recipient.

A second situation is to capture and recover certain cells from physiological fluids for research and diagnosis. Diagnostic applications may include capture and subsequent enumeration and description of captured (1) malignant cells from blood or other tissues, (2) viral or bacterially infected mammalian cells, (3) viruses or bacteria or parasites themselves from physiological fluids, (4) human fetal cells for karyotypic analysis from blood, (5) transplanted cells from blood as an index of recovery from bone marrow transplantation, and (6) immune competent cells with a particular surface marker, such as the presence of the IL-2 receptor, indicating a state of activation. For research, one may be interested in (1) the genetic analysis or modification of captured cells, (2) analysis and modification of the physiology of certain classes of cells that may be activated or suppressed by a particular disease process and (3) at the molecular level, the surface membrane compositional analysis and modification of cells involved in the pathogenesis of a particular disease.

The third situation lies in the capture and recovery of cells from physiological fluids for modification (activation) and return to the patient of origin for a desired therapeutic effect. The process involved cell capture and recovery, processing of the captured cells or depleted cell population which may result in numerical expansion and/or biological activation, and the subsequent recovery and use of these cells.

The third situation may be further divided into three levels of application. The first level is biological activation of the captured/recovered cells themselves. Activation is performed without further fractionation of the cells. For example, in the case of an AIDS patient, CD8 positive cells captured from peripheral blood can be expanded and activated for subsequent return to the patient of origin. The second level is selective activation. Captured and recovered cells are further processed or fractionated to provide a subset of captured cells, identified for example by antigen specificity, which are then activated and/or expanded. For example, certain antigen restricted subsets of the captured CD8 positive cells can be selected by certain co-culture conditions and concentrations of lymphokines, which allow only the desired subset to be expanded and activated. A third level is in vitro generation of antigen specific patient-unique cells for activation or suppression of the immune function. Exemplary of this situation is monocyte or B-cell capture and exposing the captured monocytes or B-cells to a patient-specific immune complex or other antigens under conditions which augment monocyte or B-cell antigen uptake, processing, and presentation along with increased surface MHC expression. One would then add a subset of effector or regulatory cells captured from the same patient to interact with the antigen-primed monocyte or B-cell. The process of antigen specific T-cell activation would occur, much in the manner that occurs in the lymph node of an intact animal or human. An additional example of cell modification made possible by the subject method is the introduction of exogenous genes via viral or other vectors or other means into the captured cells and the subsequent capture in a second device of the subpopulation of cells which express the exogenous gene.

The cellular source may be any mixture of cells. However, it is desired to have a predetermined population which may be defined by single or multiple markers or plurality of markers or ligands. Cellular sources of interest from animal hosts may include organs, such as blood, brain, kidney, spleen, heart, intestine, bone marrow, cerebral spinal fluid, lymphoid tissue, or the like, or neoplastic cells from any of the above organs. Other sources may be parasites, viruses or bacteria mixed with animal cells. The cells are employed in a flowable form, conveniently as a dispersion. Where the cells are not held together, as in blood, the blood will usually have red cells, platelets and plasma removed to provide for a mixture of white cells. Where the cells are held together by a membranous or other connecting material, the cells may be dispersed either mechanically or enzymatically in accordance with conventional techniques. The individual cells may then be dispersed in their appropriate nutrient medium for separation by the subject method.

With blood, red blood cells may be removed by agglutination, lysed with ammonium chloride, removed with lectins or by centrifugation in accordance with known ways. Platelets and red blood cells may also be removed by gradient density centrigation, employing Ficoll or Leukoprep and isolating the buffy coat, by centrifugation or the like.

The various cell sources may be subjected to a variety of treatments in addition to those described above. In some situations, it may be desirable to concentrate the cells by any convenient means, followed by dispersion in an appropriate nutrient medium. In some situations it may be desirable to expand a particular population, where one can selectively expand one group of cells as against another group of cells. For expansion, various mitogenic agents may be employed or interleukins, growth factors, or the like. These cells will then usually be concentrated by any convenient means to substantially remove the medium in which they have been isolated or maintained. Usually, these cells will comprise at least about 10 vol % of the dispersion to be used and not more than about 90 vol %, so as to provide a flowable dispersion. The concentration of cells introduced into the device is conveniently based upon the surface area of the derivatized polystyrene surface and will vary widely, depending upon the frequency of the target cell in the input cell suspension. Usually, the concentration will be at least $1 \times 10^3$ cells/cm$^2$ and not more than $1 \times 10^{10}$ cells/cm$^2$, usually from about $1 \times 10^5$ cells/cm$^2$ to $1 \times 10^7$/cm$^2$.

The separation device may take a wide variety of forms. For the most part, the device will be comprised of polystyrene surfaces, where the polystyrene is normally substantially free of cross-linking, less than about 0.5%, usually less than about 0.1%, preferably molded or extruded, so as to have a very smooth surface. Polystyrene surfaces of this nature allow for substantial uniformity of derivatization, where the orientation of the receptor provides for a high level of accessibility of binding sites. (It should be understood in referring to receptor, the term is entirely arbitrary. By receptor is intended a molecule which is able to specifically bind to a complementary molecule. Thus, for the purposes of this invention, the receptor may be a ligand, which includes both haptens and antigens, or a surface membrane protein which specifically binds to another molecule, such as an immunoglobulin, T-cell receptor, insulin receptor, etc., or a molecule which is found intracellularly, such as a steroid binding protein, or molecules which are found in body fluids, such as thyroxine binding globulin, lipoproteins, etc. Therefore, the membrane protein which binds specifically to the surface bound "receptor" is referred to arbitrarily as the "ligand." For convenience, they will be referred to jointly as complementary members of a specific binding pair.)

The functionalized polystyrene surface may be the surface of a wall, partition, sheet, hollow fiber, bead, particle, or the like. For the most part, it would be desirable to use a flat surface, although in some situations other surfaces may find application. The device may take the form of a bottle, standard T flask, sheets, e.g., a bag or box mith multiple separated sheets, cylindrical or serpentine sheets in a container, rectangular box, or the like. The choice of the device will depend upon convenience, the purpose of the separation, the interaction with other devices, the cell population of interest, the intended treatment, whether the population of interest is as a result of positive or negative selection, or the like.

The surface will be derivatized by substitution of the benzene ring of the polystyrene with an electrophilic reagent, particularly by a Friedel-Crafts reaction in a solvent which does not soften or dissolve the polystyrene. For this purpose, sulfolane finds particular application. Relatively mild conditions may be employed and the benzene may be derivatized with a variety of agents, such as nitro, which may be reduced to amino, halomethyl, which may be used to form an amino, hydroxy, or thiol group, or a substituted N-hydroxymethyl acetamide where the substituent is an active halogen or pseudohalogen. A description of the reaction may be found in EPA 88-304516.3.

The derivatized polystyrene surface may then be reacted with the receptor. Under the conditions of derivatization, it is found that a high percentage of the benzenes at the surface are derivatized, so that one may obtain a high density of receptor at the surface.

Depending upon the nature of the receptor, various reactions may be performed for bonding the receptor to the surface. Of particular interest is the bonding of proteins to the surface. Proteins can be bonded by contacting the proteins in an aqueous medium with the functionalized surface, having active halogen, activated carboxy groups, e.g., esters, or the like, under mild conditions for sufficient time for complete reaction. Any remaining unreacted functional groups may be blocked by using an appropriate small molecule blocking agent. For example, active halogen may be blocked with aliphatic amines, thiols with maleimide, or the like. In some situations, there may be no need to block excess reactive groups, since they will not interfere with the subsequent steps in the process. The surface may then be washed to remove the non-specifically bound receptor and evaluated to insure that appropriate receptor binding has occurred.

Depending upon the nature of the collection device, the contact with the cell containing medium will be varied. For example, with a roller bottle, one may introduce the medium into the roller bottle and then allow for slow revolution of the bottle over sufficient time for the cells to become bound. With a T-flask, or plates-in-a-bag/box configuration, one may allow the device to stand on a level surface or be slightly agitated on a shaking platform, followed by turning the device over and repeating the process on the other side. Similar techniques may be employed with other types of containers. Additionally, the device may be centrifuged to press the target cells to the contact surface.

Of particular interest, is a device which will be referred to as a collection bag/box. The bag/box will be a container of rigid or flexible walls containing polystyrene sheets superimposed or stacked one upon the other and separated from each other to allow for flow between the sheets. Packed cells as a result of concentration, e.g., gradient density centrifugation or centrifugation, would be allowed to flow into the bag/box which would be maintained in a horizontal position. The cellular dispersion would spread through the bag/box, so as to be in contact with substantially all of the receptor-coated polystyrene surface in the bag/box. After sufficient time for the cells to bind, the bag/box may be turned over so as to allow cells which are still dispersed or unbound to settle on the film surfaces which are now below them, so as to provide for efficient utilization of the surface. Alternatively, the bag/box may be centrifuged, once on each side, to press the cells to the contact surfaces.

The contact time will vary widely, depending upon the concentration of the ligand on the cell surface, the binding affinity of the receptor, the concentration of cells in the medium, the nature of the collection device, and the like. Usually contact times will be at least about 5 min and not more than about 120 min, usually from about 15 to 60 min.

The cellular dispersion may be moved through the collection device by any convenient means. A pressure differential may be achieved through the collection device by means of pumping. Alternatively, gravity flow may provide for an appropriate flow rate. Any convenient technique which allows for a rate of flow of the cells permitting binding to the surface without significantly affecting their viability may be employed.

The subject devices can be sterilized using gamma or electron beam radiation, without adversely affecting the properties of the collection device. That is, the activity of the receptor is retained, while at the same time retaining the covalent nature of its bonding to the surface. Thus, when the collection device is in use, substantially none of the receptor bound to the surface is lost.

Once the cells have become bound to the surface, the collection device may be subject to a wide variety of treatments. Vigorous washing may be employed to remove non-adherent cells, since the adherent cells are bound firmly to the surface at a plurality of contacts. The wash medium may be pumped in and out, ligands flowed through the device, or other means of mild but relatively vigorous agitation. The wash solution may be dionized water, saline, phosphate buffered saline, nutrient medium, or the like. The particular wash solution which is employed will usually depend upon how the cells are to be used.

Where the cell isolation is concerned with removal of cells from the cell population, (cell depletion), the captured cells may be discarded and the depleted cell population harvested, subjected to any additional treatments, and then used for its intended purpose.

For the most part, the subject invention finds particular application for cells which have been isolated for subsequent use. Depending upon the intended use, as well as the nature of the cells, the cells may be subjected to a wide variety of treatments. Particularly, where one is concerned with the lymphoid or myeloid lineages, these cells may be treated to expand or modify the activity of a particular set or subset of cells. Thus, various factors may be added which result in the proliferation of the cells. activation of the cells, enhancement or reduction of one or more surface membrane proteins, and the like. Depending upon whether one wishes to have all cells bound during the treatment or allow for the formation of free cells, one can provide for an appropriate ratio of receptor to bound cells in the container. By having a large number of receptors compared to the initially bound cells, any progency will also become bound and retained on the surface. This may serve as an additional resolution, since other cells which may have been present and expanded will not become bound and may be removed from the collection vessel.

For the most part, the cells of interest will be obtained from blood, bone marrow, solid tumors and lymphoid tissue. These cells may be divided into the lymphoid and myeloid lineages. The first lineage to be considered will be the lymphoid lineage. This lineage may be further broken down into categories of B-cells and T-cells. B-cells are identified by having sIg as a surface marker and rearranged germline DNA at the immunoglobulin locus. T-cells, for the most part, have CD2 and/or CD5 as surface markers and rearranged germline DNA at the T-cell receptor locus. The B- and T-cells will also include specific progenitor cells, although pluripotent stem cells will be discussed separately, and in the case of B-cells, plasma cells are also included.

Other specialized lymphoid cells which may be isolated by markers include: lymphokine activated killer (LAK) cells, natural killer (NK) cells, tumor infiltrating lymphocytes (TIL), antibody dependent cytotoxic cells (ADCC), cytotoxic T lymphocytes (CTL), etc.

In the myeloid lineage, one may be interested in isolating monocytes, macrophages, eosinophiles, basophils, polymorphonuclear leukocytes, dendritic cells, etc.

The B-cells may be expanded by treatment with various of the interleukins, 1–7 or others, when discovered, particularly IL-1, -2, -3, or the like. The B-cells may be selected by surface bound antigen, surface markers (e.g., CD20) or by specific binding to a soluble antigen, where such antigen may be added to the cells, so that those cells having a surface immunoglobulin which recognizes the antigen will bind the antigen to form a complex which is endocytosed and processed. A fragment of the antigen with the cell's MHC antigen will then be presented. By adding T-cells to the medium which are restricted by the B-cells, T-cells which recognize the antigen fragment will secrete lymphokines, resulting in proliferation of the B-cells. By providing for an excess of receptor on the solid surface or after release of the B-cells separating the cell population in a second collection device, one can substantially augment the number of B-cells and plasma cells which recognize the antigen of interest.

Alternatively, B-cell fusion partners (hybridoma cells) or other B-cells from any source can be selected by binding to a polystyrene surface which bears covalently bound antigen. Desired hybridoma or other B-cells bearing sIg reactive with polystyrene bound antigen will be captured on the polystyrene surface, allowing for antigen-specific selection of specific hybridoma or other B-cells. Captured cells can then be recovered and expanded according to the procedures described in the subject method. Alternatively T-cells or any cell containing a specific surface receptor can be captured by the polystyrene surface when said polystyrene surface contains said antigen covalently bound.

Where one wishes to deplete a specific subset of B-cells, one may add the antigen conjugated to a toxin, employ antibodies specific for the surface immunoglobulin and complement or other selective cytotoxic capability. In this way, one may selectively diminish the cells responsive to a particular antigen. Alternatively, antigen or a B-cell marker (e.g., CD-20) can be immobilized on the polystyrene and the targeted B-cell population captured on the surface. Particularly, where memory cells exist, one can reduce the homoral response by substantially depleting the memory cell population to a particular antigen.

The T-cell population is more varied than the B-cell population as to function. One may divide the mature T-cell population into CD4 MHC Class II restricted cytotoxic, helper or suppressor cells and CD8 MHC Class I restricted cytotoxic and suppressor cells, where the cells have different functions and their expansion and depletion may be of interest.

For either T-cell population (CD4 or CD8), it may be desirable to activate the T-cells which recognize a specific antigen. Many strategies can be used for this purpose. B-cells specific for a particular antigen may be exposed to that antigen and then used as antigen presenting cells to activate the particular antigen restricted T-cell subset. Alternatively, monocytes or macrophages may be employed as the antigen presenting cells. Macrophages may be preferred since they do not have the specificity of the B-cells for a particular antigen. Therefore, one would introduce monocytes and/or macrophages, which have been pre-treated or treated concomitantly with the antigen, to the bound T-cells to provide for expansion of those T-cells which recognize the antigen fragment when presented by the monocyte/macrophage in the context of the MHC.

Biological activation of cells may be achieved as a result of a particular soluble or immobilized lymphokine, e.g., IL-2, or by use of a specific binding compound, such as an antibody. For example, T-cells may be selected using an anti-T-cell (e.g., CD-5) surface. The CD-5$^+$ captured cells may then be released and introduced onto an activating anti-CD3 surface, or to a surface to which a lymphokine has been covalently bound. The cells will bind and become activated. After activation, the cells may be released by sonication, mechanical agitation or other convenient means and harvested.

Of particular interest are stem cells, which may be obtained from bone marrow or peripheral blood. These stem cells may serve as the progenitors of one or more of the blood cell lineages. Isolation of the stem cells may be as a result of both depletion (negative selection) and/or positive selection. Thus, one may provide for a series of devices or device subsections where initially the receptors will bind to undesired cells for their removal of cells (negative selection) from the medium. The unbound cells may then be isolated, freed of the captured cells and further selected (positive selection) for cells with different markers associated with stem cells, leaving a bound population of cells, which may then be freed followed by further positive selection for a marker specific for a population which includes the stem cells. In this way other cells having the analogous final marker may be removed by the previous process step.

Where cells other than blood cells are involved, cells of interest for isolation may include islets of Langerhans, glial cells, astrocytes, neurons, endothelial cells, epithelioid cells, stromal cells, stem cells, squamous cells, or the like.

Substantially homogenous populations, greater than about 95%, usually 98%, of cells may be achieved, where the cells may be in a quiescent or activated state. Cellular compositions may include any cellular population expressing a surface marker (ligand) recognized by the immobilized receptor. Such compositions include cells bearing any of the recognized leukocyte antigens of the CD (cluster designation series) or others recognized by monoclonal antibodies to specific cell surface ligands. Such compositions may include other blood cells, tumor cells, bacteria, viruses, or parasites similarly sharing a common surface marker. Virtually any cell population whose members share a surface ligand recognized by the immobilized receptor can constitute such a cellular composition.

A great variety of autoimmune, neoplastic, infectious, metabolic, hematologic and immunologic diseases and conditions, the disease field) may be treated in accordance with this invention. Among autoimmune diseases are diabetes, lupus erythematosus, and rheumatoid arthritis. Among infectious diseases are localized and systemic infections due to gram positive cocci, gram negative cocci, gram negative bacilli, anaerobic bacteria, mycobacteria, fungi, viruses, protozoa, etc. Among neoplastic diseases are all solid and hematologic malignancies. Among metabolic diseases are atherosclerosis and septic shock. Among hematologic diseases are sickle-cell anemia and familial hypercholesterol anemia. Among immunologic diseases and conditions are organ transplantation and immunodeficiency conditions.

These and other diseases or conditions may be addressed by the subject process as follows. By an alternative process, one may isolate immune complexes associated with the autoimmune infectious or neoplastic disease (see co-pending application Ser. No. 243,786, filed Sep. 13, 1988). One can use the antigen obtained from the complexes to select for both B- and T-cells as described above which are activated by the particular antigen. Thus, one can remove blood from the host suffering from the autoimmune or neoplastic disease and either selectively deplete B- and/or T-cells associated with the disease or activate T- or B-cells to suppress the autoimmune disease or to detect and eliminate the neoplastic cells. In this way, one may provide for a remission, halt the progress of the disease, or the like.

Alternatively, in cases of infection, autoimmune or neoplastic disease, one may provide for selection of B- and T-cells reactive with the particular pathogen or disease antigen. In this case, one would wish to enhance the concentration of the B- and T-cells associated with the immune defense. Thus, complexes or antigens associated with the pathogen, autoimmune or neoplastic disease or the pathogen, autoreactive or neoplastic cell itself may be used to enhance the lymphoid cellular population associated with the defense against the disease. One may isolate the pathogen, autoreactive or neoplastic cell using the subject device, and use the isolated pathogen or cell as the immunogen or receptor, as defined above to capture the appropriate T- or B-cells active in the defense against the disease. Thus selected, these cells could be recovered, expanded, activated as described above for a subsequent return to the patient of origin. This technique may be used with a wide variety of diseases associated with viruses, e.g., AIDS, HTLV-I, or II, bacteria, protozoa, fungi, helminths, and the like.

In addition, the subject method may be used for prophylactic and diagnostic purposes in the diseases field. Ths subject method will also find use in research for detecting B- and T-cell responses, investigating immune responses, identifying epitopes associated with autoimmune diseases, and ultimately used for gene therapy.

One may also use the subject device for producing monoclonal antibodies by activating B-cells, followed by immortalization of the B-cells usually by fusion with an appropriate fusion partner. In this way, one can immunize human lymphocytes against antigens one could not normally administer to a human host and provide for double selection, initially for B-cells generally, followed by selection for those specific B-cells which are capable of binding to the antigen. Thus, one can greatly concentrate B-cells specific for the antigen to greatly enchance the probability of obtaining monoclonal antibodies specific for the antigen.

The cells may be isolated from the collection device by different ways. Of particular interest is the use of a mitogenic agent, such as phytohemagglutinin (PHA), in conjunction with a compound having growth factor-like activity such as an interleukin or growth factor, e.g., interleukin-2 (IL-2), GM-CSF, etc. which results in release of the cells by shedding of the ligands on the cell surface bound to the receptor. The medium may be a standard tissue culture medium containing about 20 to 1000 units/ml IL-2 and about 0.1 to 5.0 μg/ml of phytohemagglutinin. Alternatively, the cells may be released by physical methods such as mechanical disruption, particularly shearing, such as by vibration, vigorous pipetting or by sonication using an ultrasonicator and placing the collection device in a water bath. Conveniently, a Crest ultrasonics model may be employed. See Menssen, et al., *J. Immunol. Methods* (1987) 104:1–6.

Figure 2:
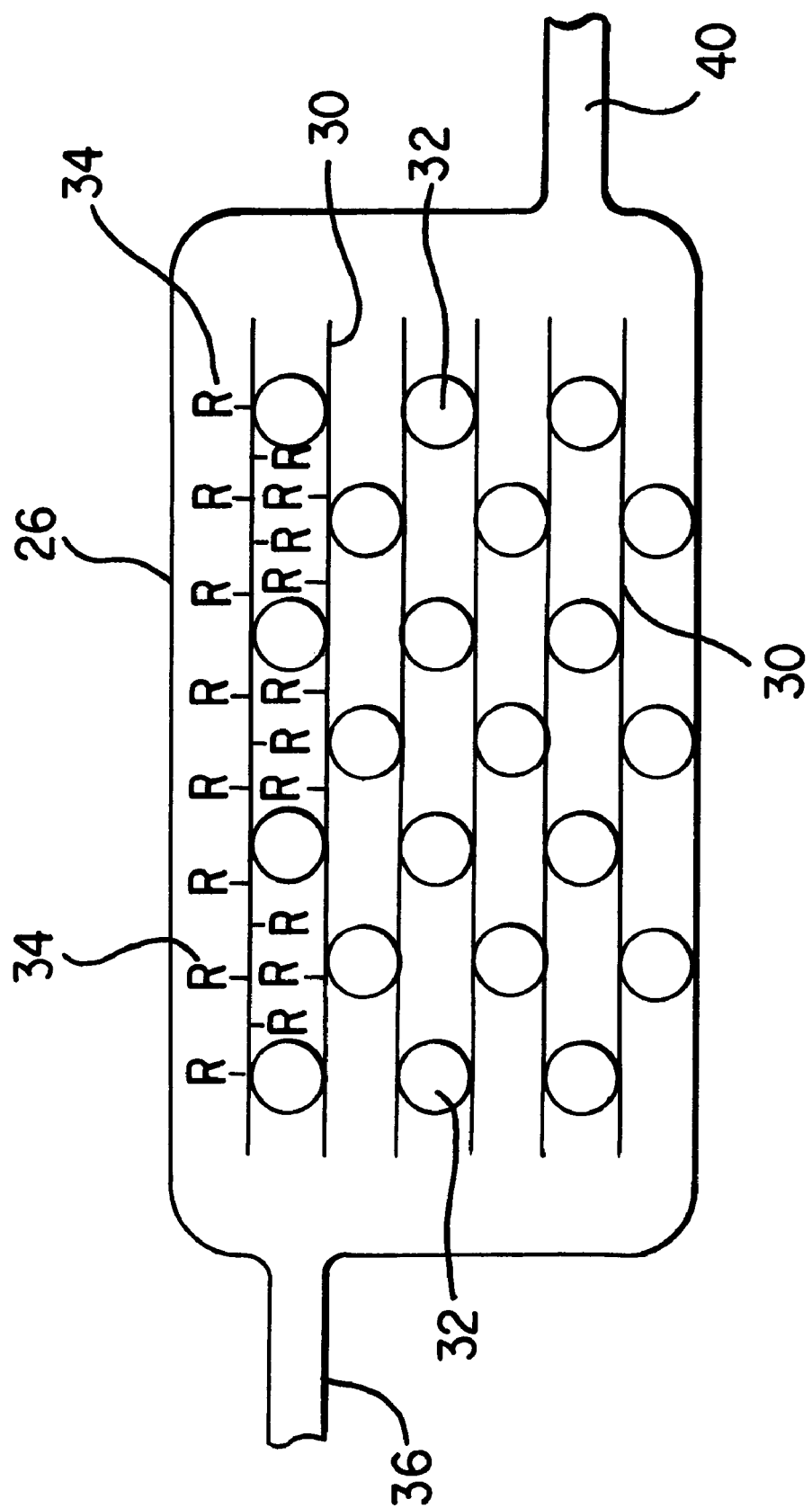
FIG. 2 is a diagrammatic view of the inside of a cell capture device.

In order to further understand the invention the figures will now be considered. FIG. 1 is a diagrammatic flowchart of a process according to the subject invention using blood as the source of target cells. The drawing involves a first stage involving the separation vessel 10, where red blood cells and platelets are removed to provide a supernatant. The supernatant 12 is then transferred to a centrifuge 14 having tubes 16, where the supernatant 12 is centrifuged to concentrate target cells 20 in the tubes 16. The target cells 20 are then transferred to a feeding vessel 22, which feeds the target cells through valve 24 into cell capture device 26, also depicted in FIG. 2. This process is not limited by the example cited. Any commonly used method to remove red blood cells, platelets and plasma can be used to achieve target cell population 20 from peripheral blood or bone marrow. Alternatively, solid tissue may be disaggregated by enzymatic or physical means to achieve target cell population 20.

Cell capture device 26 has a plurality of polystyrene films or sheets 30 separated by supports 32. On the upper films or sheets 30 are indicated the presence of receptors 34 designated as R. The receptors 34 are only indicated on a few of the films or sheets, indicating that the receptors are on both sides of the film or sheet, although it should be understood that all of the films or sheets are coated on both sides with receptors. Alternatively, the cell capture device can be a T-flask, microtiter plate, multiwell plate, roller bottle, cell farm or any other polystryrene vessel all or part of whose internal polystyrene surface has receptor immobilized to it.

The cells enter the cell capture device 26 through conduit 36. When cell capture device 26 is substantially full, it is allowed to stand for sufficient time for the cells to settle and contact the receptors on the film or sheet below the liquid layer. After sufficient time for the cells to have settled and become attached, the cell capture device 26 may then be turned over so that cells which have not become specifically bound may settle on the reverse side of the films or sheet 30 and become bound to the receptors on that side. The cell capture device may then be washed by introducing a wash solution through conduit 36 and allowing it to exit through conduit 40, so as to remove non-specifically bound cells.

One or more treatment solutions or cells suspensions may then be introduced to expand the number of captured cells, activate the captured cells, deplete a subset of the captured cells, introduce exogenous genes into the captured cells, or the like. After the treatment has been completed, the vessel may then be washed again to remove the treatment solution, cellular debris, or the like and an appropriate medium introduced to maintain the viability of the bound cells. The cells may then be released by adding a medium containing interleukin-2 and a mitogenic agent, or by taking the cell capture device 26 and introducing it into an ultrasonic bath or subjecting it to mechanical vibration or vigorous pipetting. After a short period of such physical treatment or under relatively mild sonic vibration, the captured cells are released and may be harvested.

The following examples are offered by way of illustration and not by way of limitation.

EXPERIMENTAL

I. DEVICE AND PROCESS VALIDATION

A. Synthesis of N-(hydroxymethyl) 2-bromoacetamide (HMBA) and generation of the bromoacetamide polystyrene surface (BA-PS).

HMBA is synthesized by conventional means (Leonard et al., *J. Org. Chem.* 50:2480 (1985)) from 2-bromoacetamide, available from commercial sources, in the presence of formalin at pH 10, which provides a 93% yield of the starting reactant, N-(hydroxymethyl) 2-bromoacetamide (HMBA).

The second step involves the generation of the bromoacetamide polystyrene surface (BA-PS). In this step, 2 M triflic acid and 0.2 M HMBA, both in tetramethylene sulfone (sulfolane), are mixed 1:1 in a volume sufficient to cover the inner surface of a polystyrene vessel being activated. The reaction is allowed to proceed at 27° C. for 3 hours. The reaction solution is drained, the device washed with water, followed by ethanol, and the activated polystyrene chambers are air dried. The resulting bromoacetamide polystyrene surface is stable in room air for six (6) months.

B. Cell capture surface preparation, stabilization and sterilization.

The next step is the receptor capture (the monoclonal antibody one wishes to covalently bind to the bromoacetamide-polystyrene surface). The monoclonal antibody of interest is diluted to approximately 0.01–0.05 mg/ml in phosphate buffered salin, pH 7.4. The appropriate volume of diluted monoclonal antibody is introduced into the polystyrene chamber and the reaction is allowed to proceed for from about two to twenty, preferably about 2 to 4 hours, at 27° C. with rotation. The antibody remaining after the reaction is decanted and can be re-utilized up to 10 times in subsequent coating reactions.

The antibody bound device is then washed ten times with phosphate buffered saline (PBS), pH 7.4, and the surface is then stabilized by the addition of 2% sucrose/0.2% human serum albumin (HSA), medical grade, to each device. The sucrose/albumin solution is allowed to coat the surface, after which the excess sucrose/HSA solution is decanted and the stabilized polystyrene chambers dried 24–96 hours in a vacuum (<0.10 Torr) at 25° C. After drying, the vacuum is broken with dry nitrogen and the device is flushed with inert, dry gas and capped tightly. The device is sealed and then sterilized. Sterilization is achieved by irradiation with 2.7±0.2 megarads of electron beam or gamma irradiation. Sterility tests showed that the flasks were sterile after a 14 day in situ media incubation.

C. Density of cell capture surface receptor

A variety of surface functionalization groups were employed and tested for the stability of binding of antibody to the surface. The polystyrene was functionalized using N-(hydroxymethyl)2-haloacetamide, where the halo group was chloro, bromo or iodo; diazonium and sulfonium. After monoclonal antibody attachment using these surfaces, the flasks were each washed 10 times with PBS and once with 1% SDS at 55° C. for 14 hours. The plastic surface was then assayed for radioactivity of the labeled monoclonal antibodies and the results expressed as surface density for monoclonal antibody in $ng/cm^2$. The bromoacetamide has a surface density of about 250 $ng/cm^2$ of antibody, more than 2.5 times that achieved by adsorption on an Immulon-2™ (Dynatek) surface. While the bromoacetamide provided the highest surface density, the surface density for the other functionalities fell between 200 and about 240 $ng/cm^2$.

D. Stability of capture surface receptor.

The stability of the antibody binding was determined by coating the surface with 0.02 mg/ml of ($^{35}$S) human IgG. The flasks were washed 5 times with borate-carbonate buffer, once with borate-carbonate buffer for 8 hours and twice with borate-carbonate washes over night. Aliquots of each wash were saved and assayed for radioactivity. After the second wash, there was no evidence of any antibody leaching. In a second study, using an ELISHA assay for the antibody bound to the surface, the results observed showed that the amount of extractable antibody was less than the detection limit of the assay, (7.7 ng/ml).

E. Density of cell capture by derivatized polystyrene surface.

Because the receptor-derivatized polystyrene surface retains its optical clarity, the density of the captured cells per unit area of derivatized polystyrene can be calculated by direct microscopic visualization. For most cell capture applications, the density of bound cells approaches the closest packing of spheres on a monolayer. For lymphocytes of mouse or human origin, the binding density is from $0.5 \times 10^6$ cells/cm$^2$ to $1 \times 10^6$ cells/cm$^2$. Depending upon the frequency and size of the target cell in the input cell suspension, the density of bound cells can vary widely, from $1 \times 10^3$ cells/cm$^2$ for large, rare target cells to greater than $10^{10}$ cells/cm$^2$ for small, abundant cells or particles, such as bacteria or viruses.

F. Specificity of cell capture by the derivatized polystyrene surface.

Cell binding to the functionalized polystyrene surface is specifically determined by the receptor bound to the polystyrene. The following experiment illustrates the specificity of cell binding. Mononuclear cells were prepared from peripheral blood by standard histopaque centrifugation and diluted to $3 \times 10^6$ cells/ml of PBS. An aliquot of the input was reserved for phenotype analysis by flow cytometry. The cell suspension was added to T-25 flasks which contained on their internal bottom surface, a purified monoclonal antibody covalently bound by the subject method with specificity for either (1) Thy 1.2 (a murine T-cell marker), (2) CD5, (3) CD8, or (4) an equimolar mixture of CD8 and CD5 antibodies (human T-cell markers). Cells were allowed to incubate for 30 min, then rocked gently and allowed to settle for an additional 30 min. Non-adherent cells (those not attached to the flask surface) were recovered by decanting and aliquots were also reserved for phenotype composition analyzed by flow cytometry. In all cases, except the Thy 1.2 flask in which no cells were seen bound to the flask, microscopic examination of the flasks showed confluent cell binding, at a density of $0.5 \times 10^6$ cells/cm$^2$. Flow cytometric analysis was performed on all input and efflux (non-adherent) cell populations for the markers CD5, CD8 (human T-cells), CD14 (human moncytes), CD16 (human NK-cells) and CD20 (human B-cells) and the relative frequencies of these markers in input and efflux compared for each flask. The results show no differences between input and efflux for the Thy 1.2 flask. The CD5 and CD8 flasks showed respectively, greater than 98% depletion of CD5 and CD8 cells in the efflux, and the CD5/8 flask showed depletion of CD5 and CD8 cells to a degree equivalent to that of either the monospecific CD5 or CD8 flask. The markers for moncytes and NK-cells and B-cells showed relative enrichment in the efflux as they were not captured by the flask. These data show that (1) cells are quantitatively and specifically captured by the cell capture device, (2) the functionalized surface does not exhibit non-specific cell binding, and (3) more than one cell phenotype can be captured simultaneously by a bi-derivatized polystyrene surface.

G. Process for cell recovery from the capture device.

Two techniques were employed to recover cells from the capture device. Both show quantitative cell recovery, good viability, absence of monoclonal antibody on the surface of the recovered cells and full biological activity for both replication and function. The first method, called lymphokine release, was tested with $CD8^{30}$ cytotoxic T-cells captured from normal human peripheral blood according to the subject method described above. After decanting of the non-adherent cells and verifying confluent binding by microscopic observation, standard tissue culture media supplemented with recombinant IL-2 (300 units/ml) (usually between 20 and 1000 units/ml) and phytohemagglutinin (PHA:Gibco 0.1 mg/ml) (usually between 0.1 and 5.0 mg/ml) were added. After 48 to 72 hours of culture, the captured $CD8^+$ cells spontaneously detach from the flask, leaving all the monoclonal antibody covalently attached to the polystyrene surface.

The captured CD8 cells were shown to be free of surface-bound monoclonal antibody by flow cytometry analysis using fluoresceinated anti-mouse antibody. None of the released $CD8^+$ cells were positive for surface mouse IgG. Furthermore, the flask can be re-used for cell capture by washing in PBS containing 4 M MgCl which regenerates the capture surface. Such re-used flasks perform consistently for 4-6 cycles after which repeated washing reduces the bound antibody activity. Further proof of retention of the antibody by the polystyrene surface is provided by in situ polystyrene blotting studies in which radiolabeled anti-mouse antibody is reacted with the derivatized polystyrene, washed vigorously and the surface either assayed by autoradiography or by direct scintillation counting. In both sets of experiments, the polystyrene surface is fully saturated with bound monoclonal antibody indicating retention of the antibody in the device.

The detached cells, recovered by decanting, can be expanded numerically in standard tissue culture chambers supplemented with IL-2 and phytohemagglutinin. Viability by Trypan blue exclusion was shown to be greater than 98% and the recovered, homogeneous cell population could be expanded by two orders of magnitude over a period of about 10 days.

The second method for cell recovery, called ultrasonic release, utilizes an ultrasonic bath (Crest Ultrasonics model #H-4HT-1014-6) with an output of 40 to 90 kHz sonic output (main frequency at 40 kHz) evenly distributed through a water bath by means of the Crest Vibra-bar. The power supply delivers 500 watts at 40 to 90 kHz. The ultrasonic bath has an immersion tank of 10×14 inches, holding a volume of 6 gallons of fluid which contained one liter (0.5" from the tank bottom) for sonication in the subjection studies. Immersion tanks of various sizes are commercially available. The capture device containing the bound cells is immersed in the one liter of fluid in the ultrasonic bath and the power supply and power application time experimentally determined. Depending upon the cell phenotype, times and powers varied: For example, $CD4^+$ T-cells: 78% max power, 17 sec; $CD8^+$ T-cells: 30% max power, 20 sec; Leu 19 cells: 75% max power, 10 sec, etc.

To demonstrate that the cells recovered by sonication were still viable and retained their physiological activity, $CD16^+$ NK-cells were recovered by sonication at maximum power for 15 to 20 seconds. The cells recovered by sonication (1) were greater than 85% viable by Trypan blue exclusion, and (2) were extremely active in a lytic assay routinely utilized to quantitate NK-cell activity. Using flow cytometric analysis, cells recovered by sonication were shown to be free of monoclonal antibody, as were cells recovered by the mitogen/lymphokine drive method described above. Thus, in cells recovered by both methods, the antibody remains behind when the cells are recovered, providing viable, homogeneous, fully functional cells free of monoclonal antibody.

H. Phenotypic homogeneity of released cells.

Previously (section F) analysis of input and efflux (non-captured) cell phenotypes showed that cell binding by the cell capture device is specified by the monoclonal antibody covalently bound to the device surface. In this section, data are presented to confirm and extend these findings by analyzing by flow cytometry the cells recovered from the device by lymphokine release. Mononuclear cells from peripheral blood of normal human volunteers were prepared by standard histopaque centrifugation as described and introduced at a concentration of $3 \times 10^6$ cells/ml PBS into cell capture devices containing either CD8 or CD4 monoclonal antibody covalently bound to the inner surface. After standard incubation and decanting of non-attached cells, the captured cells were recovered by incubation for 48 hours with IL-2 and PHA as described in section G. The recovered cells were then phenotyped by flow cytometry and cultured in standard culture media supplemented with IL-2 and PHA. Aliquots of cells were sampled periodically over 6-25 days in culture for flow cytometric analysis. The data show greater than 95% homogeneity for $CD4^+$ and $CD8^+$ surface markers on recovered cells from the CD4 and CD8 devices, respectively, at time zero (immediately after recovery from the device). More importantly, as the recovered cells logarithmically grow in culture, their phenotypic homogeneity is preserved, with cultures maintaining greater than 95% purity for CD4 and CD8 markers, respectively, over the 6-25 day culture period. Released cells are therefore homogenous in phenotype and their homogeneity is maintained during in vitro logarithmic growth.

I. Numerical expansion of released cells.

$CD8^+$ cells recovered by lymphokine drive from a CD8 capture device using human peripheral blood mononuclear cells from six (6) different individuals were cultured in standard culture media supplemented with IL-2 and and PHA (300 units/ml and 0.1 $\mu$g/ml, respectively) in standard culture vessels in a humidified incubator at 37° C. Cells were sampled for viability by Trypan blue exclusion and cell number by hemocytometer counting periodically over 25 days of culture. Each individual's cells were kept separated from the others. The data show greater than 95% cell viability and a two log increase in cell number over 20 days. These data demonstrate the capability of cells recovered from the capture device to exponentially expand in number in standard tissue culture.

J. Induction of proliferation of recovered cells by immobilized CD3 monoclonal antibody.

In this study, $CD8^+$ cells harvested from peripheral blood of normal volunteers were captured in the subject device containing CD8 antibody and recovered by lymphokine drive. The recovered cells were then cultured in either standard tissue culture flasks using standard tissue culture medium supplemented with recombinant IL-2 and PHA, or cultured in the subject device with covalently-bound anti-CD3 monoclonal antibody using standard medium without supplementation with either recombinant IL-2 or PHA. Duplicate flasks with the anti-CD3 monoclonal antibody were employed. At time zero, equal numbers of cells were loaded, respectively, into flasks A, B and C (A=standard tissue culture flask with IL-2/PHA supplemented media; B and C=CD3 subject device without IL2 or PHA). After five days in culture, each culture was split into two aliquots and replated in identical flasks under identical culture conditions. Cells were then recounted at day 9, resulting in the following fold-expansions between days 5 and 9: A:2.7; B:2.55; C:6.75. Control cultures in which $CD8^+$ cells were cultured in standard tissue culture vessels without IL-2 or PHA supplement failed to grow at all. Thus, cell expansion was achieved at the same or greater multiple using immobilized anti-CD3 antibody and the subject device as compared to IL-2/PHA supplemented media in a standard tissue culture flask. These data demonstrate that by immobilizing a T-cell activating monoclonal antibody (CD3) to the polystyrene surface according to the subject method, T-cell activation/proliferation can be achieved by the immobilized monoclonal in the absence of soluble activation factors (IL-2/PHA) in the culture medium.

II. SPECIFIC EXAMPLES

A. Bone marrow transplantation.

In this first example, T-cell depletion for bone marrow transplantation is exemplified. Data indicate that the $CD5^+$ and $CD8^+$ T-cells which are present in bone marrow material cause graft-versus-host disease. A device as described above was prepared using monoclonal antibodies to CD5 and CD8 positive human T-cells. Aliquots of human bone marrow obtained from normal human volunteers were introduced into a subject device and the cells incubated as described. Non-adherent cells were recovered, phenotyped and subjected to in vitro cultures to quantitate enrichment for progenitor cells compared to input non-fractioned marrow. The following tables indicate typical results.

TABLE 1

| Depletion of T-cells (%depletionofinput) | | | | | |
|---|---|---|---|---|---|
| CD5 | CD8 | CD4 | CD14 | CD16 | CD19 |
| 91 | 96 | 65 | −129 | −29 | 4 |

TABLE 2

| EnrichmentofProgenitors (% enrichment over input) | | | | |
|---|---|---|---|---|
| CFU-EU | BFU-E | CFU-GM | CFU-M | CFU-G |
| 513 | 633 | 376 | 311 | 244 |

CFU-EU = colony forming units, erythroid units
BFU-E = burst forming units, erythroid
CFU-GM = colony forming units, granulocyte-monocyte
CFU-M = colony forming units, monocyte
CFU-G = colony forming units, granulocyte The data in the tables show specific depletion of $CD5^+$ and CD8 cells ($CD14^+$, $CD16^+$ cells are enriched, $CD19^+$ cells are unchanged) and 2–6-fold enrichment for progenitor cells. These data illustrate the use of the subject method to specifically deplete cells causing graft-versus-host disease while enriching for the desired progenitor cells.

In the second example of bone marrow transplantation applications, the ability of the subject device to concentrate a particular rare cell population in a mixture of cells from bone marrow or peripheral blood is demonstrated. The cells to be concentrated are progenitor stem cells from human bone marrow. In this example, the subject device incorporates a CD34 monoclonal antibody covalently bound to the polystyrene surface. In the first case of this example, human bone marrow samples were introduced into the CD34 subject device, the cells incubated as described, the non-adherent cells recovered by decanting and the captured cells recovered by sonication. The three fractions, input, non-adherent and adherent cells, were assayed for CFU-C, a standard assay for progenitor cells. The following table shows the results:

TABLE 3

| | CFU-C/25,000 Cells |
|---|---|
| Input cells | 3 |
| Non-adherent cells | 0 |
| Adherent cells | 44 |

The data indicate a 15-fold increase in progenitor cells achieved by the subject device and the subject method of cell recovery by sonication.

In the second case of this example, peripheral blood mononuclear cells were introduced into another CD34 subject device. Non-adherent cells were recovered by decanting, adherent cells were again recovered by sonication. Aliquots of the input and adherent cells were analyzed for $CD34^+$ phenotype. The input cells were less than 0.1% positive for $CD34^+$ cells. The adherent cells recovered by sonication were 15% $CD34^+$ indicating the utility of the subject device and method for recovering viable progenitor cells from peripheral blood.

B. Anti viral cellular therapy, e.g., AIDS

In the next example, a process for the treatment of viral infection, e.g., AIDS, is exemplified. The techniques is to expand $CD8^+$ cells by capturing $CD8^+$ cytotoxic T-cells from peripheral blood mononuclear cells. The captured $CD8^+$ cells are then recovered by a brief culture in medium containing a lectin and recombinant IL-2 (lymphokine drive), followed by expansion of the detached cells in standard tissue culture vessels for 14 to 28 days prior to final washing and collection for reinfusion into the patient of origin.

Specifically, peripheral blood human mononuclear cell (PBMC) concentrated with Ficoll-Hypaque were introduced into a T-150 polystyrene flask with a anti-CD8 monoclonal antibody covalently attached. After one hour of incubation, the blood was decanted and tissue culture medium supplemented with IL-2(300 unit/ml) and PHA (0.1 $\mu$g/ml). After 48–72 hours of culture, the $CD8^+$ cells spontaneously detach from the flask leaving the antibody covalently attached to the surface of the polystyrene as demonstrated by flow cytometric analysis showing the absence of monoclonal antibody on the surface of the detached cells. The detached cells are then expanded in a standard tissue culture chambers supplemented with IL-2 and PHA as above.

Analysis by flow cytometry showed the population to be 100% positive for CD3 and 98% positive for CD8 cell surface markers. The phenotype of the captured cells is consistent with the description reported for cytotoxic lymphocytes bearing the CD8 surface marker.

Captured $CD8^+$ cells from six healthy donors were shown to grow logarithmically for up to 15–36 days in culture with the media containing IL-2 and PHA as above. Analysis of the cells during growth at days 7, 10, 15 and 25, show that the $CD3^+$, $CD8^+$ phenotype was persistent (greater than 98% positive) throughout the 25 days expansion. In a lectin-dependent cellular cytotoxicity assay using convanavalin A-coated-CEM cells, the composite lytic activity of cells from five different normal donors was determined. Substantial lysis was observed at effector-to-target ratios ranging from 2.5 to 10. These same $CD8^+$ cells after expansion show no lysis of normal autologous PBMC from healthy donors. Thus, these cells have normal cytotoxic activity to appropriate target cells, while lacking autoimmune cytotoxic activity.

These cells were investigated to determine whether they had undergone changes which might make them susceptible to immune attack by autologous PBMCs. The results of two experiments from different donors in which the donor PMBC response to chromium-labeled self and non-self CD8 cells were examined showed that lysis occurred only for non-self $CD8^+$ cells after in vitro priming with non-labeled, non-self $CD8^+$ cells. Thus, the $CD8^+$ cells do not undergo surface phenotype alterations which after reinfusion into the patient of origin, might render them targets for an autoimmune process.

These cells were shown to retain antigen-specific, MHC restricted cytolytic activity after isolation and expansion. $CD8^+$ cells were harvested from EBV (Epstein Barr virus)-positive healthy donors and tested for specific cytotoxicity against chromium-labeled EBV-infected mitomycin C-treated autologous B-cells. During co-cultivation, reduced doses of IL-2 were added to the medium to allow for the selective expansion of $CD8^+$ cells with specific reactivity against EBV-infected MHC restricted autologous B-cells. The protocol for this assay was to include a control in which $CD^+$ cells were grown but not primed and then subjected to the chromium release assay on day 9 and thereafter. The experiment included: (1) an aliquot of cells subjected to the chromium release assay on day 0 before priming, (2) another aliquot primed on day 0, primed again on day 7, and then subjected to the chromium release assay on day 9 and thereafter. The results were as follows: (1) $CD8^+$ cells not exposed to EBV-transformed autologous B-cells showed no lytic activity, (2) control cultures utilizing $CD8^+$ cells from EBV-sero-negative healthy donors also showed no lytic activity whether primed or not primed, (3) with primed $CD8^+$ cells from EBV-sero-positive donors, at effector:target ratios in the range of 3 to 12.5, percent specific lysis ranged from 25 to about 45. These results demonstrate that the $CD8^+$ cells harvested and expanded after 14 days of cold culture demonstrate antigen-specific MHC restricted cellular cytotoxicity appropriate to the antigenic milieu of the host.

In the next study, $CD8^+$ cells were obtained from HIV-positive volunteers. The cells were harvested from Ficoll-Hypaque PBMC as described above, captured with a CD8 subject device and recovered by lymphokine release as described. Logarithmic growth for 18 days in culture with nearly 100% viability was achieved with $CD8^+$ cells from HIV-positive donors. The $CD8^+$ phenotype was substantially retained (greater than 95% positive CD8) during in vitro expansion. These cells exhibited appropriate cytotoxicity against lectin coated CEM cells and exhibited no NK-like lytic activity against K562 targets. In addition, the $CD8^+$ cell showed no suppressor activity in a B-cell immunoglobulin synthesis assay. The cells are not transformed, requiring constant IL-2 to remain in growth phase. The cells do not produce HIV virus and, after washing, are lymphokine, PHA and monoclonal antibody free.

The expanded $CD8^+$ cells showed stable phenotype, normal lytic activity, maintained the absence of markers for other types of cells, and were capable of cytolytic activity against appropriate target cells. Most importantly, these $CD8^+$ cells exhibited an inhibition of autologous HIV virus replication in vitro. This was established by combining $CD4^+$ cells infected with HIV with autologous expanded $CD8^+$ cells. Complete repression of HIV replication was achieved at as low a CD4:CD8 ratio as 1:0.25 after 7 days. Different time periods and different CD4:CD8 ratios were involved with different donors, but in all cases, HIV repression was complete in the autologous setting, lasting for up to 35 days in culture (the longest period tested).

In summary, these data show that $CD8^+$ cells captured from PBMCs by the subject method and recovered by lymphokine drive: (1) are phenotypically pure, (2) are capable of exponential growth in vitro, (3) are phoenotypically stable during exponential growth, (4) are capable of potent, appropriate cytotoxic activity, (5) are capable of repressing HIV replication in autologous $CD4^+$ cells when the $CD8^+$ cells are captured from HIV seropositive donors, (6) show, in general, MHC and antigen restricted cytotoxicity, (7) show no autoreactivity, (8) show no auto recognition, (9) show no suppressor cell activity, (10) are not transformed, (11) do not produce HIV virus, and (12) do not retain residual biologicals derived from the culture process after washing. These cells are suitable for a variety of therapeutic applications, including AIDS, cytomegalovirus infections, EBV infections, toxoplasmosis infections, etc. Furthermore, the $CD8^+$ cells, when isolated by the subject method from tumors or lymphoid homogenates from cancer patients, show substantial anti-cancer activity, as shown in the next example.

C. Tumor infiltrating lymphocyte.

Cell suspensions obtained by enzymatic digestion of tumors or lymphoid tissue from cancer patients were introduced into devices containing CD4 or CD8 monoclonal antibody bound to the surface. After capturing the $CD4^+$ or $CD8^+$ cells and recovering them by either sonication or lymphokine drive, the recovered cells were shown to be greater than 98% viable and greater than 95% phenotypically pure $CD4^+$ or $CD8^+$ cells, respectively. In all cases examined, either the purified $CD4^+$ or purified $CD8^+$ cells exhibited at least as much autologous tumor cytotoxicity as the unseparated starting tissue suspension. The purified population did not exhibit non-specific killing of allogeneic tumor. The purified population were capable of logarithmic growth, maintaining viability, phenotypic homogeneity and autologous tumor cytotoxicity. The phenotype of the cytotoxic cell varied among tumor types, $CD8^+$ predominating for melanoma and squamous cell carcinoma, $CD4^+$ predominating for renal cell carcinoma.

D. Lymphokine activated killer cells (LAK).

In the next example, anti-CD5, anti-CD14 and anti-CD20 monoclonal antibodies were employed in subject devices to deplete PBMCs to enrich by negative selection for NK-cells. The antibodies were shown to be capable of depletion of the $CD5^+$ phenotype by greater than about 98%, the $CD14^+$ phenotype by greater than 50% and the $CD20^+$ phenotype by greater than 90%. To obtain LAK cells, $1.5 \times 10^8$ mononuclear cells were added to the collection device containing CD5 monoclonal antibody. After incubating for 30 min, the non-adherent cells were recovered by decanting, and transferred to a device containing covalently bound anti-CD14 antibody. After incubation, the non-adherent cells were again recovered by decanting and transferred to a third device, this one containing CD20 monoclonal antibody covalently bound to the surface. Incubation was again for 30 min at room temperature. The third population non-adherent cells were then cultured in IL-2 for 48 to 72 hours and their lytic activity assayed in standard 4-hour chromium release assays using K562 for NK activity and COLO-205 cells for LAK activity. The percent specific lysis for different effector to target ratios was determined where the effector to target ratio varied from 2.5 to 20. Using cells from several different normal donors, the enrichment of LAK activity varied from 50% to 300% over input cells cultured under identical conditions.

The cell population derived from the subject device was shown to be substantially enriched for LAK precursors, virtually free of T- and B-cells and significantly depleted of monocytes. The phenotype of the LAK precursor purified by the subject device was found to be CD3⁻, CD16⁺ and Leu 19⁺.

In the next study, the question of whether the lytic unit activity was increased out of proportion of the phenotypic enrichment of NK cells in the purified samples was addressed. The lytic units were calculated for the input and purified fractions per $10^6$ NK effector cells. A 2 to 50-fold increase in lytic units per $10^6$ NK effector cells is achieved with the three step monoclonal antibody negative depletion method described. This established that the monocyte, B-cell, T-cell depletion protocol increased by a factor of 2 to 50, the lytic unit activity expressed per NK effector cell. This increase is achieved by the removal of other cells that directly or indirectly exert inhibitory influences on LAK activity. See Nii, et al., *Int. J. Cancer* (1988) 41:33–40; Hoyer, et al., *Cancer Res.* (1986) 46:2834–2938. These authors report the down regulation by activated autologous monocytes of human lymphokine IL-2 activated killer cell activity. The subject procedure achieved a 90% reduction in total cell number resulting in the saving of culture resources required to perform the NK activation; and a 2 to 50-fold augmentation in lytic activity expressed on a per-NK effector cell basis.

The data presented above demonstrate that the subject methodology improves the efficacy of IL-2/LAK therapy, decreases the cost of the therapy, and reduces the toxicity of the procedure by lowering the total number of cells obtained by leukapheresis necessary to generate the targeted total lytic activity for re-infusion after IL-2 activation.

E. Suppressor-inducer cells

In a similar manner to the previous procedures, the monoclonal antibody 2H4 which binds to the suppressor/inducer cell, a cell which induces specific suppressor cells, can be utilized to harvest, recover, activate and expand suppressor/inducer cells to treat autoimmune disease. The suppressor/inducer cell would be positively selected from PBMCs, recovered from the collection device by sonication, expanded and activated numerically according to the prior procedures. These expanded and activated suppressor/inducer cells could then be reinfused to the patient of origin with the autoimmune disease in question, which would result in the induction of suppressor cell activity appropriate to the patient's pathophysiology.

The above results demonstrate the power of the subject device and process in isolating a wide variety of cells with different surface markers. The procedures may be used in research, diagnosis and therapy. Furthermore, the procedure allows for collection, expansion and activation of cells while retaining a very high percentage of viability of the cells. In addition, antigenic components of blood or tissue may be taken from a patient, such as immune complexes or tumor cells or normal tissue and used to activate or deactivate specific responses to an antigen or cell. Thus, cellular responses may be provided to a wide variety of diseases, including: genetic diseases, where stem cells may be transfected so as to modify their phenotype; autoimmune diseases, where suppressor cells may be used to suppress an immune response; cancer and viral diseases where killer cells may be used in their treatment; and pathogen derived diseases where helper and B-cells may be used in protection against a wide variety of pathogens.

F. Polystyrene Fiber-Based Separation Devices

Results of the testing of devices utilizing pads composed of fibers showed generally equivalent performance to flat plate separation devices. However, the fibers are superior in some respects, e.g., in that more CD34⁺ cells were recovered after a CD⅝ depletion with a fiber pad than from a similar depletion with an Applied Immune Sciences T3000 flat plate device. Additionally, it is easier to work with fiber-pad devices because they permit the used smaller devices that take advantage of the high surface area of fiber pads in comparison to flat plates. Moreover, processing time and associated steps are reduced.

In preparing fiber pad devices, pre-made polystyrene (DOW 685D) fibers are shot into a box, where pads are formed as the polystyrene fiber is felted and needlepunched to tangle them into a mass. Five to seven fibers were utilized, but the procedure can be followed with as few as one fiber. The fibers utilized were about 80 microns in diameter; with fibers ranging from about 70–100 microns. After compression between two heated plates to form pads, the pads were cut to shape and then compressed again between two heated plates. The mean space between fibers was roughly 1,250 microns. One skilled in the art can optimize the pad size and fiber composition to optimize its performance. The derivatization and functionalization steps thereafter are the same as those applied to flat plate polystyrene.

White blood cells were prepared for separation on the device by conventional techniques. A peripheral blood leukopak (e.g., a bag containing leukophoresis products) was ficolled, resulting in at least $1.2 \times 10^{10}$ cells. Peripheral blood was treated with Dulbecco's Phosphate Buffered Saline Solution with EDTA (D-PBSE), and no more than $1 \times 10^{10}$ cells were treated in each of separate tubes. A 35 ml aliquot of diluted blood was placed into 50 ml conical tubes. Each tube was underlaid with 10 ml of Isopaque® and centrifuged for 20 minutes at about 2300 rpm (1092×g).

The plasma layer was then collected and the mononuclear layer at the interface was collected and placed into a 50 ml conical tube and made up with 50 ml D-PBSE. These tubes were centrifuged for 20 minutes at 2000 rpm (826×g). The Ficoll®-separated cells were washed for 5 minutes at 2000 rpm, again using D-PBSE. A sample of the Ficolled PBSC were collected for cell counts and fluorescence-activated cell sorting. The peripheral blood stem cells (PBSC) were resuspended in 1% autologous plasma and an aliquot of $10 \times 10^6$ cells was prepared as a sample input for phenotyping. Platelets were removed by diluting the cells 1:5 in the leukopak bag and centrifuging at about 900 rpm (180×g) for 20 minutes. The platelet-rich plasma fraction was removed, leaving about 60 ml of cells.

These cells were resuspended at a concentration of about $8.3 \times 10^7$ white blood cells (WBC)/ml in D-PBSE/CMF and $10 \times 10^6$ cells were retained as input cells for phenotyping.

The fiber device itself was assembled from sheets of polycarbonate, clamped together, with inlet and outlet ports added. A comparison run with a T3000 AIS CELLector®, prepared by the methods disclosed above, was conducted.

TABLE 4

Comparison of T Depletion on 3000 and Fibers

|  | 5/8 | Log D CD5 | % D CD5 | Both Devices Log D CD34 | % D CD34 | Serial Passes Log D CD8 | % D CD8 | Log D CD19 | % D CD19 |
|---|---|---|---|---|---|---|---|---|---|
| n = 19 | 3000 | 1.1 | 92.4 | 0.4 | 60.2 | 0.8 | 84.0 | 0.4 | 59.5 |
| n = 16 | FIBER | 1.1 | 92.1 | 0.1 | 8.0 | 0.9 | 88.2 | 0.3 | 54.3 |

G. Use of Fiber Pads in Series $3 \times 10^9$ cells were loaded into a CD5/CD8 pad in a rigid plastic container. The cell load volume was 12 ml, followed by a 6 ml D-PBSE chase. The device was incubated for one and one-half hours vertically with a flip at 40 and 65 minutes. The fiber was washed at the rate of 30 ml/min with three column volumes of D-PBSE. The nonadherent cells were collected, volume measured, cells counted and a sample retained for flow analysis. The remaining sample was divided into three equal aliquots. These nonadherent cells were loaded into three separate pads, with one-third of the nonadherent cells being introduced into each CD5/CD8 pad in a rigid plastic container. For each device, again, cell load volume was about 12 ml followed by a 6 ml D-PBSE chase. The devices were incubated for one and one-half hours in a vertical position but flipped at 40 and 65 minutes. Washing again at 30 ml/min with 3 column volumes of D-PBSE. The nonadherent cells were collected, volume measured and cells counted, with the remainder retained as a sample for flow analysis. All cell fractions were counted with a Cobas Helios® cell counting device. Flow analysis on input and nonadherent samples was performed using the Bekton/Dickinson FACScan® cell counter.

All publications and patent applications cited in this specification are herein incorporated by reference as if each individual publication or patent application were specifically and individually indicated to be incorporated by reference.

Although the foregoing invention has been described in some detail by way of illustration and example for purposed of clarity of understanding, it will be readily apparent to those of ordinary skill in the art in light of the teachings of this invention that certain changes and modifications may be made thereto without departing from the spirit or scope of the appended claims.

What is claimed is:

1. A method for preparing a separated cell population from a mixture of cells, comprising:
    (a) contacting said mixture of cells with a device comprising at least one, optically clear polystyrene film or sheet, internal to the device, having support having a plurality receptors covalently bound to both flat surfaces thereof, which device has the following properties:
        (i) the covalent bonding is produced by derivatizing the benzene rings of polystyrene which is less than 0.5% crosslinked;
        (ii) the receptors are at a density of between about 200 ng receptor per $cm^2$ surface area and about 250 ng receptor per $cm^2$ surface; and
        (iii) the receptors bind specifically to at least one cell-surface ligand,
    said contacting being for sufficient time for cells bearing said ligand to bind specifically to said receptors on said flat surfaces, resulting in specifically bound cells and unbound cells;
    (b) removing said unbound cells from said device without significantly disturbing the binding of said specifically bound cells to said surface such that said bound cells remain bound to said device; and
    (c) releasing said bound cells from said device such that released cells are free of said receptors,
    thereby preparing said separated cell population.

2. A method according to claim 1, wherein said receptors are bound to said polystyrene through acetamido linkages.

3. A method for preparing a separated cell population from a mixture of cells, comprising:
    (a) contacting said mixture of cells with a device comprising at least one, optically clear polystyrene film or sheet, internal to the device, having receptors covalently bound to both flat surfaces thereof, which device has the following properties:
        (i) the covalent bonding is produced by derivatizing the benzene rings of polystyrene which is less than 0.5% crosslinked with a substituted N-hyroxymethyl acetamide having a substituent selected from the group consisting of chloro, bromo, iodo, diazonium and sulfonium,
        (ii) the receptors are specific for at least one ligand present on the surface of said cells,
    said contacting being for sufficient time for said cells to bind specifically to said receptors on said flat surfaces, resulting in specifically bound cells and unbound cells;
    (b) removing said unbound cells from said device without significantly disturbing the binding of said specifically bound cells to said surface such that said bound cells remain bound to said device; and
    (c) releasing said bound cells from said device such that released cells are free of said receptors,
    thereby preparing said separated cell population.

4. A method according to claim 3, wherein said derivatizing is with N-(hyroxymethyl)-2-bromoacetamide.

5. The method of claim 1 or 3, wherein said cell surface ligand is a membrane protein.

6. A method according to claim 1 or 3, wherein said releasing step comprises incubating said bound cells in the presence of a mitogenic agent or a combination of a mitogenic agent and an interleukin or growth factor.

7. A method according to claim 1 or 3, wherein said bound cells are hematopoietic cells.

8. A method according to claim 7, further comprising the step of:
    (d) contacting said specifically bound and released hematopoietic cells with
        (i) one or more of the following cell activating agents: (A) an antigen, (B) an interleukin, (C) a cell that binds to a surface protein of said released cells, (D) an immune complex, (E) a mitogen and (F) an activating antibody;

(ii) a transfection vector;
(iii) a cytotoxic agent; or
(iv) a combination of any of (i), (ii) and (iii).

9. A method according to claim 7, wherein said specifically bound and released cells are lymphoid cells and said activating agent is an interleukin.

10. A method according to claim 7 wherein said receptor is a monoclonal antibody.

11. A method according to claim 10, wherein said monoclonal antibody is specific for at least one lymphocyte marker which is a cell-surface protein.

12. A method according to claim 11, wherein said lymphocyte marker is a T-cell marker.

13. A method according to claim 12, wherein said T-cell marker is a cytotoxic T-cell marker.

14. A method according to claim 13 which additionally comprises, prior to said releasing step (c), a step of activating said bound cytotoxic T-cells by incubating in said device with an immune complex, an activating antibody, an antigen or antigen-presenting cells expressing the appropriate MHC proteins to which said cytotoxic T-cells are restricted.

15. A method according to claim 11, wherein said lymphocyte marker is a B-cell marker and said bound cells are B-cells.

16. A method according to claim 15 comprising, prior to said releasing step (c), a step of activating said bound B-cells by adding to said B cells in said device a population of T helper cells restricted appropriately to MHC proteins of said B-cells.

17. A method according to claim 10, wherein said polystyrene has less than 0.1% crosslinking.

18. A method according to claim 7, wherein said hematopoietic cells are myeloid cells.

19. A method according to claim 7 wherein said polystyrene has less than 0.1% crosslinking.

20. A method according to claim 1 or 3, further comprising after step (c):

(d) contacting said released cells with a second device which comprises a second group of receptors covalently bonded to a polystyrene surface as recited in step (a), which receptors are specific for a second cell surface ligand or ligands different from the ligand or ligands of step (a), said contacting being for sufficient time for said released cells to bind specifically to said receptors of said second group;

(e) removing unbound and non-specifically bound cells from the specifically bound cells of step (d) without significantly disturbing the binding of said cells bound via said second ligand; and (f) releasing said bound cells of step (d) from said second device such that released cells are free of said receptors of said second group.

21. A method for preparing a homogeneous population of activated T-cells in accordance with claim 20, wherein (i) said cell mixture in step (a) comprises peripheral blood mononuclear cells;

(ii) said receptors in step (a) comprise monoclonal antibodies specific for a T cell marker;

(iii) said releasing of bound T cells from said antibodies in step (c) is by sonication or mechanical vibration;

(iv) said second device contains covalently bound activating anti-CD3 monoclonal antibodies, and said T cells are incubated in said second device for a time sufficient to allow said T cells to become activated by said anti-CD3 antibodies; and (v) in step (f), said bound and activated T-cells are released from said device by sonication or mechanical vibration, thereby preparing said homogeneous population of activated T-cells.

22. The method of claim 20 wherein said first cell-surface ligand is selected from the group consisting of CD4, CD8, and CD34 and second cell surface ligand is CD4 or CD8.

23. A method according to claim 20, wherein said polystyrene has less than 0.1% crosslinking.

24. A method according to claim 1 or 3, further comprising after step (c), a negative selection process which comprises:

(d) contacting said released cells with a second device which comprises a second group of receptors covalently bonded to a polystyrene surface as recited in step (a), which receptors are specific for a second cell surface ligand or ligands different from the ligand or ligands of step (a), said contacting being for sufficient time for said released cells to bind specifically to said receptors of said second group;

(e) collecting unbound cells from said second device without significantly disturbing the binding of cells bound via said second ligand to obtain cells that are free of cells that specifically bound to said second receptors.

25. The method of claim 24 wherein said surface ligand in said first or second device is CD4 or CD8.

26. A method according to claim 24, wherein said polystyrene has less than 0.1% crosslinking.

27. The method of claim 1 or 3 wherein said cell-surface ligand is CD4, CD8 or CD34.

28. A method according to claim 1 or 3, wherein said polystyrene has less than 0.1% crosslinking.

* * * * *